US 8,504,142 B2

(12) United States Patent
Tikkanen et al.

(10) Patent No.: US 8,504,142 B2
(45) Date of Patent: Aug. 6, 2013

(54) APPARATUS, METHOD, AND COMPUTER PROGRAM FOR PREDICTING RISK FOR CARDIAC DEATH

(75) Inventors: Jani Tikkanen, Oulu (FI); Heikki Huikuri, Oulu (FI); Tuomas Kenttä, Kempele (FI); Mari Karsikas, Oulu (FI); Tapio Seppänen, Oulu (FI)

(73) Assignee: Oulun yliopisto, Oulu (FI)

( * ) Notice: Subject to any disclaimer, the term of this patent is extended or adjusted under 35 U.S.C. 154(b) by 309 days.

(21) Appl. No.: 12/945,387

(22) Filed: Nov. 12, 2010

(65) Prior Publication Data

US 2012/0123283 A1    May 17, 2012

(51) Int. Cl.
*A61B 5/0452* (2006.01)

(52) U.S. Cl.
USPC ........................................................ 600/509

(58) Field of Classification Search
USPC ........................................................ 600/509
See application file for complete search history.

(56) References Cited

U.S. PATENT DOCUMENTS

| | | |
|---|---|---|
| 6,358,214 B1 | 3/2002 | Tereschouk |
| 2009/0137916 A1* | 5/2009 | Maison-Blanche et al. ... 600/516 |

OTHER PUBLICATIONS

Antzelevitch, C. et al., "Brugada Syndrome: Report of the Second Consensus Conference," *Heart Rhythm*, 2: 429-440 (2005).
Bianco, M. et al., "Does Early Repolarization in the Athlete Have Analogies with the Brugada Syndrome?" *European Heart Journal*, 22: 504-510 (2001).
Bjornstad, H. et al., "Electrocardiographic Findings According to Level of Fitness and Sport Activity," *Cardiology*, 83: 268-279 (1993).
Cappato, R. et al., "J Wave, QRS Slurring, and ST Elevation in Athletes with Cardiac Arrest in the Absence of Heart Disease: Marker of Risk or Innocent Bystander?" *Circ Arrhythm Electrophysiol*, 3: 305-311 (2010).
Crouse, S.F. et al., "Electrocardiograms of Collegiate Football Athletes," *Clin Cardiol*, 32(1): 37-42 (2009).
Greene, H.L. et al., "Classification of Deaths After Myocardial Infarction as Arrhythmic or Nonarrhythmic (The Cardiac Arrhythmia Pilot Study)," *The American Journal of Cardiology*, 63(1): 1-6 (1989).
Haissaguerre, M. et al., "Sudden Cardiac Arrest Associated with Early Repolarization," *N Engl J Med*, 358(19): 2016-2023 (2008).
Huikuri, H., "Long-term Prognosis of Early Repolarization in General Population," Cardiostim 2010, Jun. 16-19, Nice Acropolis—French Riviera (Conference Presentation).
Junttila, M.J. et al., "Prevalence and Prognosis of Subjects with Brugada-type ECG Pattern in a Young and Middle-Aged Finnish Population," *European Heart Journal*, 25: 874-878 (2004).

(Continued)

*Primary Examiner* — Scott Getzow
*Assistant Examiner* — Amanda Patton
(74) *Attorney, Agent, or Firm* — Hamilton, Brook, Smith & Reynolds, P.C.

(57) ABSTRACT

An apparatus, a method, and a computer program for predicting a risk for a cardiac death are presented. Early repolarization patterns in leads of an electrocardiogram recorded from a subject are detected if an amplitude of a J-point at a QRS complex and ST segment junction of a lead exceeds a predetermined amplitude threshold. Amplitude patterns of ST segments in leads of the electrocardiogram are also determined. Finally, an elevated risk for a future cardiac death of the subject on the basis of a possible arrhythmia is predicted if early repolarization patterns are detected in at least two leads of the electrocardiogram, and if the ST segments in the at least two leads of the electrocardiogram are determined to have a horizontal or descending amplitude pattern.

16 Claims, 15 Drawing Sheets

(56) References Cited

OTHER PUBLICATIONS

Klatsky, A.L. et al., "The Early Repolarization Normal Variant Electrocardiogram: Correlates and Consequences," *Am J Med*, 115: 171-177 (2003).

Matsuo, K. et al., "The Prevalence, Incidence and Prognostic Value of the Brugada-Type Electrocardiogram," *Journal of the American College of Cardiology*, 38(3): 765-770 (2001).

Merchant, F.M. et al., "Ability of Terminal QRS Notching to Distinguish Benign from Malignant Electrocardiographic Forms of Early Repolarization," *Am J Cardiol*, 104: 1402-1406 (2009).

Miyasaka, Y. et al., "Prevalence and Mortality of the Brugada-Type Electrocardiogram in One City in Japan," *Journal of the American College of Cardiology*, 38: 771-774 (2001).

Nam, G.B. et al., "Augmentation of J Waves and Electrical Storms in Patients with Early Repolarization," *N Engl J Med*, 358(19): 2078-2079 (May 8, 2008).

Pajuno, P. et al., "The Validity of the Finnish Hospital Discharge Register and Causes of Death Register Data on Coronary Heart Disease," *Eur J Cardiovasc Prev Rehabil*, 12: 132-137 (2005).

Pelliccia, A. et al., "Prevalence of Abnormal Electrocardiograms in a Large, Unselected Population Undergoing Pre-Participation Cardiovascular Screening," *Eur Heart J*, 28: 2006-2010 (2007).

Reunanen, A. et al., "The Social Insurance Institution's Coronary Heart Disease Study. Baseline Data and 5-Year Mortality Experience," *Acta Med Scand Suppl*, 673: 1-120 (1983).

Rosso, R. et al., "J-Point Elevation in Survivors of Primary Ventricular Fibrillation and Matched Control Subjects," *Journal of the American College of Cardiology*, 52: 1231-1238 (2008).

Shipley, R.A. et al., "The Four-Lead Electrocardiogram in Two Hundred Normal Men and Women," *Am Heart J*, 11: 325-345 (1936).

Sinner, M.F. et al., "Association of Early Repolarization Pattern on ECG with Risk of Cardiac and All-Cause Mortality: A Population-Based Prospective Cohort Study (MONICA/KORA)," *PLoS Medicine*, 7(7): e1000314 (Jul. 2010).

Tikkanen, J.T. et al., "Long-Term Outcome Associated with Early Repolarization on Electrocardiography," *N Engl J Med*, 361: 2529-2537 (2009).

\* cited by examiner

|  | No ER | ER + | P-value |
|---|---|---|---|
| No. of subjects | 35 | 27 |  |
| Age | 13.3±0.6 | 13.4±0.6 | NS |
| Males (%) | 100 | 100 | NS |
| Heart rate (bpm) | 71±17 | 68±11 | NS |
| QRS duration (ms) | 88±8 | 84±12 | 0.02 |
| QTc interval (ms) | 405±17 | 417±22 | 0.02 |
| PR-interval (ms) | 145±25 | 142±20 | NS |
| LVH (%)* | 20.6 | 55.2 | 0.004 |
| Sokolow-Lyon index (mV) | 3.1±0.7 | 3.6±0.7 | 0.01 |
| QRS-angle (degrees) | 71±21 | 74±47 | NS |
| J-point amplitude (mV) | 0 | 0.13±0.03 | <0.001 |

*Left ventricular hypertrophy defined as Sokolow-Lyon index > 3.5mV

± values are means SD

FIG. 9

| | No ER | ER with Type I S-T | ER with Type II S-T | P-value[1] | P-value[2] | P-value[3] |
|---|---|---|---|---|---|---|
| No. of subjects | 352 | 16 | 91 | | | |
| Males (%) | 48 | 62 | 62 | NS | 0.02 | NS |
| Heart rate (bpm) | 62 ± 11 | 59 ± 8 | 60 ± 9 | NS | NS | NS |
| QTc interval (ms) | 393 ± 29 | 398 ± 22 | 390 ± 26 | NS | NS | NS |
| LVH (%)* | 12.4 | 25.0 | 30.3 | NS | <0.001 | NS |
| Sokolow-Lyon index (mV) | 2.5 ± 0.8 | 2.8 ± 1.2 | 3.1 ± 0.9 | NS | <0.001 | NS |

*Left ventricular hypertrophy defined as Sokolow-Lyon index > 3.5mV
± values are means SD
[1]P-value between ER type I and no ER; [2]P-value between ER type II and no ER; [3]P-value between ER type I and II.
Analysis performed with one way ANOVA in continuous variables and separately with chi-square in categorical variables.
Missing ER type info on 44 ER carriers.

FIG. 10

|  | No ER<br>N=10288 | ER with Type II S-T<br>N=164 | ER with Type I S-T<br>N=412 | P Value for Difference<br>(No vs ER with Type II S-T) | P Value for Difference<br>(No vs ER with Type I S-T) |
|---|---|---|---|---|---|
| Males (%)* | 51.5 | 88.1 | 57.1 | <0.001 | 0.03 |
| Age (years)† | 44.0 ± 8.5 | 42.6 ± 7.9 | 45.5 ± 8.2 | 0.04 | <0.001 |
| Current smoker (%)‡ | 33.8 | 38.4 | 36.4 | 0.17 | 0.20 |
| Cholesterol (mmol/l) ‡ | 6.50 ± 1.32 | 6.48 ± 1.32 | 6.58 ± 1.21 | 0.84 | 0.22 |
| BMI (kg/m²) ‡ | 25.9 ± 3.9 | 25.0 ± 2.9 | 25.7 ± 3.6 | 0.001 | 0.15 |
| Heart rate (bpm) ‡ | 76 ± 15 | 70 ± 12 | 75 ± 14 | <0.001 | 0.09 |
| Systolic blood pressure (mmHg) ‡ | 138 ± 22 | 134 ± 16 | 138 ± 21 | 0.01 | 0.62 |
| Diastolic blood pressure (mmHg) ‡ | 82 ± 12 | 79 ± 12 | 83 ± 13 | <0.001 | 0.61 |
| Chronotropic medication (%) ‡ | 4.3 | 3.2 | 4.2 | 0.46 | 0.89 |
| Cardiovascular disease (%) ‡ | 8.1 | 8.7 | 7.2 | 0.75 | 0.49 |
| Electrocardiographic LVH (%) ‡ | 30.8 | 60.6 | 33.2 | <0.001 | 0.27 |
| QTc duration (ms) ‡ | 408 ± 28 | 400 ± 22 | 409 ± 28 | <0.001 | 0.86 |
| QRS duration (ms) ‡ | 87 ± 8 | 87 ± 7 | 89 ± 7 | 0.31 | <0.001 |
| ECG signs of coronary artery disease (%) ‡ | 9.6 | 12.2 | 14.9 | 0.35 | 0.71 |
| History of prior myocardial infarction (%) ‡ | 1.1 | 0.3 | 1.3 | 0.35 | 0.71 |
| History of angina pectoris (%) ‡ | 2.3 | 2.5 | 1.6 | 0.85 | 0.33 |

* Adjusted for age; † Adjusted for sex; ‡ Adjusted for age and sex; ± values are means SD
ER type 1 = ≥0.1mV J-point elevation in inferior and/or lateral leads + dominant horizontal/descending ST-segment
ER type 2 = ≥0.1mV J-point elevation in inferior and/or lateral leads + dominant rapidly ascending ST-segment

FIG. 11

| According to ST-segment | No. | Unadjusted RR | Adjusted RR* |
|---|---|---|---|
| Type 1 – ST-segment horizontal / descending: | | | |
| Any J-point type ER ≥0.1mV in inferior and/or lateral leads | 412 | 1.62 (1.19-2.21) | 1.43 (1.05-1.94) |
| Any J-point type ER >0.2mV in inferior and/or lateral leads | 50 | 3.37 (1.75-6.51) | 2.61 (1.35-5.04) |
| Inferior any J-point type ER ≥0.1mV | 265 | 2.01 (1.43-2.82) | 1.72 (1.22-2.41) |
| Inferior any J-point type ER >0.2mV | 33 | 4.28 (2.13-8.58) | 3.14 (1.56-6.30) |
| Inferior notched ER ≥0.1mV | 133 | 2.38 (1.51-3.76) | 1.60 (1.01-2.53) |
| Inferior slurred ER ≥0.1mV | 127 | 1.63 (0.98-2.72) | 1.76 (1.06-2.94) |
| Inferior slurred ER >0.2mV | 13 | 4.72 (1.77-12.61) | 5.26 (1.97-14.07) |
| Lateral any J-point type ER ≥0.1mV | 142 | 0.92 (0.46-1.85) | 0.84 (0.42-1.70) |
| Lateral any J-point type ER >0.2mV | 17 | 1.26 (0.18-8.93) | 1.11 (0.16-7.91) |
| Type 2 – ST-segment rapidly ascending: | | | |
| Any J-point type ER ≥0.1mV in inferior and/or lateral leads | 164 | 1.15 (0.67-2.00) | 0.89 (0.52-1.55) |
| Any J-point type ER >0.2mV in inferior and/or lateral leads | 10 | 1.66 (0.23-11.84) | 1.08 (0.15-7.69) |
| Inferior any J-point type ER ≥0.1mV | 90 | 1.31 (0.65-2.63) | 1.01 (0.50-2.03) |
| Inferior any J-point type ER >0.2mV | 3 | No deaths | No deaths |
| Inferior notched ER ≥0.1mV | 23 | 1.55 (0.39-6.17) | 1.34 (0.33-5.39) |
| Inferior slurred ER ≥0.1mV | 41 | 1.53 (0.57-4.10) | 1.02 (0.38-2.74) |
| Lateral any J-point type ER ≥0.1mV | 124 | 1.02 (0.52-1.95) | 0.84 (0.43-1.60) |

| According to J-point type (independent of ST-segments) | No. | Unadjusted RR | Adjusted RR* |
|---|---|---|---|
| J-point notched type: | | | |
| Notched type ER ≥0.1mV in inferior and/or lateral leads | 215 | 2.00 (1.37-2.94) | 1.58 (1.07-2.32) |
| Notched type ER >0.2mV in inferior and/or lateral leads | 30 | 2.87 (1.19-6.91) | 2.14 (0.89-5.16) |
| Inferior notched ER ≥0.1mV | 158 | 2.23 (1.45-3.44) | 1.54 (1.00-2.38) |
| Inferior notched ER >0.2mV | 22 | 3.44 (1.29-9.18) | 2.10 (0.79-5.62) |
| Lateral notched ER ≥0.1mV | 65 | 1.57 (0.75-3.30) | 1.70 (0.80-3.58) |
| J-point slurred type: | | | |
| Slurred type ER ≥0.1mV in inferior and/or lateral leads | 290 | 1.31 (0.89-1.94) | 1.19 (0.81-1.76) |
| Slurred type ER >0.2mV in inferior and/or lateral leads | 30 | 3.29 (1.37-7.93) | 2.46 (1.02-5.92) |
| Inferior slurred ER ≥0.1mV | 171 | 1.56 (1.01-2.50) | 1.50 (0.95-2.37) |
| Inferior slurred ER >0.2mV | 14 | 4.59 (1.72-12.26) | 5.14 (1.92-13.76) |
| Lateral slurred ER ≥0.1mV | 134 | 0.79 (0.38-1.67) | 0.68 (0.32-1.44) |

*Adjusted for age and sex

FIG. 12

APPARATUS, METHOD, AND COMPUTER PROGRAM FOR PREDICTING RISK FOR CARDIAC DEATH

TECHNICAL FIELD

The invention relates to predicting a risk for a cardiac death on the basis of an electrocardiogram analysis. An appropriate apparatus, method, and computer program are disclosed for the analysis.

BACKGROUND

Heart disease is the leading cause of death in most industrialized nations. Health care is able to treat and manage cardiovascular illnesses in a surprisingly effective fashion. However, the prerequisite is that the persons at risk are identified. Various tests have been developed, but due to the dire consequences of the disease, it is well worth the effort to continue the refinement of the methodology with which the risk for a cardiac death may be assessed.

Electrical instabilities in the heart are known to characterize or indicate a potential for abnormal conditions, which may result in sudden cardiac death (SCD). Sudden cardiac death is defined as an unexpected natural death from a cardiac cause within a short time period, generally $\leq 1$ h from onset of symptoms, in a person without prior condition that would appear to result in instantaneous fatality. The majority of SCD events are associated with a structurally diseased heart. It has been estimated that only 3 to 10% of patients who have an out-of-hospital cardiac arrest are successfully resuscitated.

For decades, early repolarization (ER), which is characterized by an elevation of the junction between the end of the QRS complex and the beginning of the ST segment (i.e. J-point) from baseline on standard 12-lead electrocardiography (ECG, EKG), has been considered to be an innocuous finding in healthy persons, see Klatsky et al Am J Med 2003 115: 171-177.

The prevalence of ER in the general population varies from less than 1% to 13%, depending on age, race, sex, and the criterion for J-point elevation. Earlier, diagnosis of ER has not been considered relevant to the proposed prognosis in case of healthy subjects.

However, the presence of this pattern in leads other than V1 through V3 (especially in the inferior leads) has recently been associated with vulnerability to ventricular fibrillation in independent case-control studies, see Haissaguerre et al N Engl J Med 2008 358: 2016-2023, Nam et al N Engl J Med 2008 358: 2078-2079, and Rosso et al J Am Coll Cardiol 2008 52: 1231-1238. Furthermore, it is not clear whether all types of ER in inferior and/or lateral leads are associated with increased risk of life-threatening arrhythmias.

SUMMARY

The present invention seeks to provide an improved apparatus, an improved method, and an improved computer program for predicting a risk for a cardiac death.

According to an aspect of the present invention, there is provided an apparatus comprising a processor configured to detect early repolarization patterns in leads of an electrocardiogram recorded from a subject if an amplitude of a J-point at a QRS complex and ST segment junction of a lead exceeds a predetermined amplitude threshold, determine amplitude patterns of ST segments in leads of the electrocardiogram and predict an elevated risk for a future cardiac death of the subject on the basis of a possible arrhythmia if early repolarization patterns are detected in at least two leads of the electrocardiogram, and if the ST segments in the at least two leads of the electrocardiogram are determined to have a horizontal or descending amplitude pattern.

According to another aspect of the present invention, there is provided a method performed in an electronic apparatus comprising detecting early repolarization patterns in leads of an electrocardiogram recorded from a subject if an amplitude of a J-point at a QRS complex and ST segment junction of a lead exceeds a predetermined amplitude threshold, determining amplitude patterns of ST segments in leads of the electrocardiogram and predicting an elevated risk for a future cardiac death of the subject on the basis of a possible arrhythmia if early repolarization patterns are detected in at least two leads of the electrocardiogram, and if the ST segments in the at least two leads of the electrocardiogram are determined to have a horizontal or descending amplitude pattern.

According to another aspect of the present invention, there is provided a computer program comprising program instructions which, when loaded into an apparatus, cause the apparatus to detect early repolarization patterns in leads of an electrocardiogram recorded from a subject if an amplitude of a J-point at a QRS complex and ST segment junction of a lead exceeds a predetermined amplitude threshold to determine amplitude patterns of ST segments in leads of the electrocardiogram and to predict an elevated risk for a future cardiac death of the subject on the basis of a possible arrhythmia if early repolarization patterns are detected in at least two leads of the electrocardiogram, and if the ST segments in the at least two leads of the electrocardiogram are determined to have a horizontal or descending amplitude pattern.

According to another aspect of the present invention, there is provided another apparatus apparatus comprising means for detecting early repolarization patterns in leads of an electrocardiogram recorded from a subject if an amplitude of a J-point at a QRS complex and ST segment junction of a lead exceeds a predetermined amplitude threshold, means for determining amplitude patterns of ST segments in leads of the electrocardiogram and means for predicting an elevated risk for a future cardiac death of the subject on the basis of a possible arrhythmia if early repolarization patterns are detected in at least two leads of the electrocardiogram, and if the ST segments in the at least two leads of the electrocardiogram are determined to have a horizontal or descending amplitude pattern.

BRIEF DESCRIPTION OF THE DRAWINGS

Embodiments of the present invention are described below, by way of example only, with reference to the accompanying drawings, in which

FIGS. 9, 10, 11, 12, 13, 14, and 15 illustrate a study on the described embodiments.

DETAILED DESCRIPTION

The following publication is incorporated herein by reference: Tikkanen J T, Anttonen O, Junttila M J, Aro A L, Kerola T, Rissanen H A, Reunanen A, Huikuri H V. Long-term outcome associated with early repolarization on electrocardiography. N Engl J Med. 2009; 361: 2529-2537.

Also the following conference presentation is incorporated herein by reference: Huikuri H V. Long-term prognosis of early repolarization in general population. Cardiostim 2010 Jun. 16-19, Nice Acropolis—French Riviera.

The following embodiments are exemplary. Although the specification may refer to "an" embodiment in several locations, this does not necessarily mean that each such reference is to the same embodiment(s), or that the feature only applies to a single embodiment. Single features of different embodiments may also be combined to provide other embodiments.

Figure 7:
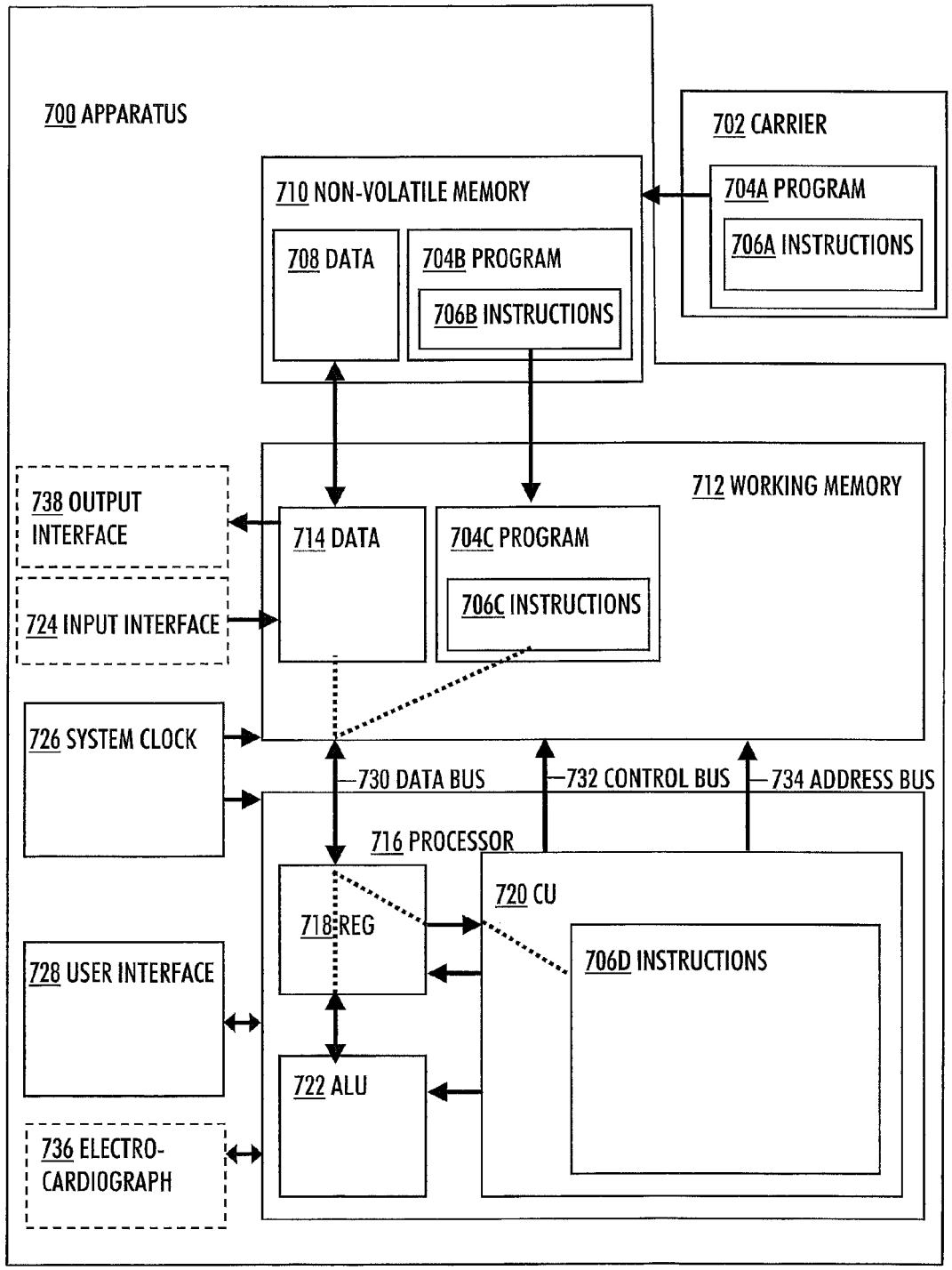
FIG. 7 illustrates embodiments of an apparatus.

FIG. 7 illustrates embodiments of an apparatus 700. FIG. 7 only shows some elements whose implementation may differ from what is shown. The connections shown in FIG. 7 are logical connections; the actual physical connections may be different. Interfaces between the various elements may be implemented with suitable interface technologies, such as a message interface, a method interface, a sub-routine call interface, a block interface, or any means enabling communication between functional sub-units. It should be appreciated that the apparatus 700 may comprise other parts. However, such other parts may be irrelevant to the actual invention and, therefore, they need not be discussed in more detail here. It is also to be noted that although some elements are depicted as separate ones, some of them may be integrated into a single physical element. The specifications of the apparatus 700 may develop rapidly. Such development may require extra changes to an embodiment. Therefore, all words and expressions should be interpreted broadly, and they are intended to illustrate, not to restrict, the embodiments.

The apparatus 700 comprises a processor 716. The processor 716 is configured to detect early repolarization (ER) patterns in leads of an electrocardiogram (ECG, EKG) recorded from a subject if an amplitude of a J-point at a QRS complex and ST segment junction of a lead exceeds a predetermined amplitude threshold. The processor 716 is also configured to determine amplitude patterns of ST segments in leads of the electrocardiogram. The processor 716 is also configured to predict an elevated risk for a future cardiac death of the subject on the basis of a possible arrhythmia if early repolarization patterns are detected in at least two leads of the electrocardiogram, and if the ST segments in the at least two leads of the electrocardiogram are determined to have a horizontal or descending amplitude pattern.

In an embodiment, the leads are inferior leads II, III, and aVF of a 12-lead electrocardiogram, and/or the leads are lateral leads I, aVL, V4, V5, and V6 of the 12-lead electrocardiogram. In an embodiment, the prediction of the elevated risk requires that the early repolarization patterns are detected and the ST segments are determined to have the horizontal or descending amplitude pattern in the same lead location category, i.e. the at least two leads are detected within the inferior leads, or the at least two leads are detected within the lateral leads. It appears that such case, wherein one lead tested positive belongs to the inferior leads and the other lead tested positive belongs to the lateral leads, does not necessarily predict the elevated risk.

In an embodiment, the amplitude threshold is at least one of 0.08 millivolts, over 0.08 millivolts, between 0.08 and 0.12 millivolts, 0.1 millivolt, over 0.1 millivolt, between 0.18 and 0.22 millivolts, over 0.18 millivolts, 0.2 millivolts, over 0.2 millivolts, between 0.08 and 0.22 millivolts.

Even further processing of the electrocardiogram may be beneficial. Consequently, in an embodiment, the processor 716 may further be configured to: categorize the J-points in leads where early repolarization patterns were detected; and predict an elevated risk for a future cardiac death of the subject on the basis of a possible arrhythmia if early repolarization patterns are detected in at least two leads of the electrocardiogram, and if the ST segments in the at least two leads of the electrocardiogram are determined to have a horizontal or descending amplitude pattern, and if the J-points in the at least two leads of the electrocardiogram are categorized as notched or slurred.

Next, we will describe the structure of the apparatus 700 in more detail, and, upon this, we will describe the processing of the ECG in more detail.

The apparatus 700 may be an electronic digital computer, which may comprise, besides the processor 716, a working memory 712, and a system clock 726. Furthermore, the computer 700 may comprise a number of peripheral devices. In FIG. 7, some peripheral devices are illustrated: a non-volatile memory 710, an input interface 724, and a user interface 728 (such as a pointing device, a keyboard, a display, a touch screen etc.). Naturally, the computer 700 may comprise a number of other peripheral devices, not illustrated here for the sake of clarity.

The user interface 728 may be used for user interaction: a physician may view the ECG with the user interface 728, and a predicted risk for a cardiac death may be shown to the physician with the user interface 728. In an embodiment, the apparatus 700 further comprises an output interface 738 configured to output the predicted elevated risk for the future cardiac death of the subject. The output interface 738 may be the user interface 728, but it may also be some other type of interface capable of outputting data even to another apparatus or a system, such as a communications interface, operating in a wired or wireless fashion, for example.

The system clock 726 constantly generates a stream of electrical pulses, which cause the various transferring operations within the computer to take place in an orderly manner and with specific timing.

Depending on the processing power needed, the computer 700 may comprise several (parallel) processors 716, or the required processing may be distributed amongst a number of computers 700. The computer 700 may be a laptop computer, a personal computer, a server computer, a mainframe computer, or any other suitable computer. As the processing power of portable communications terminals, such as mobile phones, is constantly increasing, the apparatus 700 functionality may be implemented into them as well. Besides the contemporary computers utilizing binary digits, bits, for representing data and instructions by the use of the Binary number system's two-binary digits "0" and "1", the emerging quantum computers may also be used, such quantum computers utilizing quantum bits, qubits, instead of bits.

In some cases, it may be so that there really is one physical apparatus 700 for implementing the embodiments. But, this is just one option. The apparatus 700 may be implemented as a single computer, a distributed apparatus, a group of computers implementing the structure and functionality of the apparatus 700, or a group of distributed parts implementing the structure and functionality of apparatus 700. The apparatus 700 may also be implemented as a server of a service provider. The electrocardiogram may be transmitted from a clinic to the server 700. The transmission of the electrocardiogram to the server 700 may be implemented in a wired and/or wireless fashion, such as over a local area network (LAN), over Ethernet, over Internet, and/or utilizing radio transceivers such as short-range radio transceivers, or cellular radio transceivers, for example, or by any other suitable communications means. Depending on the scale of the whole system, the functionalities may also be distributed over a number of front-end clients implementing a part of the apparatus 700 functionality, and at least one back-end server implementing a part of the apparatus 700 functionality as well. A peer-to-peer network structure may be utilized in some cases to implement a suitable network of interacting apparatuses.

It is to be noted that the apparatus 700 functionality may be implemented, besides in computers, in other suitable data processing equipment as well: in an electrocardiograph, or in an other device recording and/or analyzing ECG data. Consequently, the apparatus 700 may comprise an electrocardiograph 736 configured to record the electrocardiogram from the subject with electrodes. The implementation of the apparatus 700 functionality may also comprise both specific equipment, such as electrocardiographs, and general computers, such as stand-alone computers or clients and servers.

The electrocardiograph 736, by definition, is an instrument used in the detection and diagnosis of heart abnormalities that measures electrical potentials on the body surface of the subject with electrodes and generates the electrocardiogram as a record of the electrical currents associated with heart muscle activity.

In order to produce an electrocardiogram, usually ten skin electrodes are placed on the subject: one electrode for each wrist, one electrode for each ankle, and six electrodes for the chest. Wires connecting the electrodes to the electrocardiograph 736 may be called leads, but we use the more common definition: a 'lead' refers to a combination of electrodes that form an imaginary line in the body along which the electronic signal are measured. In this discussion, we refer to a 12-lead electrocardiograph, but the embodiments are not restricted to an electrocardiogram produced with such an electrocardiograph. Indeed, the standard 12-lead electrocardiogram may be produced from Frank's vectorcardiographic XYZ lead system, they may be derived from other types of leads, or they may be produced by any means capable of being transformed into the standard 12-lead electrocardiogram presentation. Additionally, the embodiments may be applicable to other kind of electrocardiogram lead sets besides the standard 12-lead electrocardiogram. U.S. Pat. No. 6,358,214, incorporated herein by reference, discloses an ECG scanner operating in a three-dimensional space formed by synthesized ECG leads, and the embodiments may be applied in such an implementation as well.

If the apparatus 700 is not capable of producing the electrocardiogram by itself, the apparatus 700 may further comprise an input interface 724 configured to receive the electrocardiogram recorded from the subject. The electrocardiogram may thus have been recorded minutes, hours, days, months, or even years earlier. Alternatively, the electrocardiogram may be recorded in real-time, but not necessarily with the apparatus 700, but with another apparatus comprising the electrocardiograph. In both cases, the input interface 724 may be used to bring the recorded electrocardiogram into the apparatus 700.

The term 'processor' refers to a device that is capable of processing data. The processor 716 may comprise an electronic circuit or electronic circuits implementing the required functionality, and/or a microprocessor or microprocessors running a computer program 704C implementing the required functionality. When designing the implementation, a person skilled in the art will consider the requirements set for the size and power consumption of the apparatus 700, the necessary processing capacity, production costs, and production volumes, for example. The electronic circuit may comprise logic components, standard integrated circuits, application-specific integrated circuits (ASIC), and/or other suitable electronic structures.

The microprocessor 716 implements functions of a central processing unit (CPU) on an integrated circuit. The CPU 716 is a logic machine executing a computer program 704C, which comprises program instructions 706C. The program instructions 706C may be coded as a computer program using a programming language, which may be a high-level programming language, such as C, or Java, or a low-level programming language, such as a machine language, or an assembler. The CPU 716 may comprise a set of registers 718, an arithmetic logic unit (ALU) 722, and a control unit (CU) 720. The control unit 720 is controlled by a sequence of program instructions 706D transferred to the CPU 716 from the working memory 712. The control unit 720 may contain a number of microinstructions for basic operations. The implementation of the microinstructions may vary, depending on the CPU 716 design. The microprocessor 716 may also have an operating system (a general purpose operating system, a dedicated operating system of an embedded system, or a real-time operating system, for example), which may provide the computer program 704C with system services.

There may be three different types of buses between the working memory 712 and the processor 716: a data bus 730, a control bus 732, and an address bus 734. The control unit 720 uses the control bus 732 to set the working memory 712 in two states, one for writing data into the working memory 712, and the other for reading data from the working memory 712. The control unit 720 uses the address bus 734 to send to the working memory 712 address signals for addressing specified portions of the memory in writing and reading states. The data bus 730 is used to transfer data 714 from the working memory 712 to the processor 716 and from the processor 716 to the working memory 712, and to transfer the instructions 706C from the working memory 712 to the processor 716.

The working memory 712 may be implemented as a random-access memory (RAM), where the information is lost after the power is switched off. The RAM is capable of returning any piece of data in a constant time, regardless of its physical location and whether or not it is related to the previous piece of data. The data may comprise ECG, any temporary data needed during the analysis, program instructions etc.

The non-volatile memory 710 retains the stored information even when not powered. Examples of non-volatile memory include read-only memory (ROM), flash memory, magnetic computer storage devices such as hard disk drives, and optical discs. As is shown in FIG. 7, the non-volatile memory 710 may store both data 708 and a computer program 704B comprising program instructions 706B.

An embodiment provides a non-transitory computer readable storage medium 702 storing a computer program 704A, comprising program instructions 706A which, when loaded into an apparatus 700, cause the apparatus 700 to detect early repolarization patterns in leads of an electrocardiogram recorded from a subject if an amplitude of a J-point at a QRS complex and ST segment junction of a lead exceeds a predetermined amplitude threshold; to determine amplitude patterns of ST segments in leads of the electrocardiogram; and to predict an elevated risk for a future cardiac death of the subject on the basis of a possible arrhythmia if early repolarization patterns are detected in at least two leads of the electrocardiogram, and if the ST segments in the at least two leads of the electrocardiogram are determined to have a horizontal or descending amplitude pattern.

The computer program 704A may be in source code form, object code form, or in some intermediate form. The computer program 704A may be stored in a carrier 702, which may be any entity or device capable of carrying the program to the apparatus 700. The carrier 702 may be implemented as follows, for example: the computer program 704A may be embodied on a record medium, stored in a computer memory, embodied in a read-only memory, carried on an electrical carrier signal, carried on a telecommunications signal, and/or embodied on a software distribution medium. In some jurisdictions, depending on the legislation and the patent practice, the carrier 702 may not be the telecommunications signal.

FIG. 7 illustrates that the carrier 702 may be coupled with the apparatus 700, whereupon the program 704A comprising the program instructions 706A is transferred into the non-volatile memory 710 of the apparatus. The program 704B with its program instructions 706B may be loaded from the non-volatile memory 710 into the working memory 712. During running of the program 704C, the program instructions 706C are transferred via the data bus from the working memory 712 into the control unit 720, wherein usually a portion of the instructions 706D resides and controls the operation of the apparatus 700.

There are many ways to structure the program 704A/704B/704C. The operations of the program may be divided into functional modules, sub-routines, methods, classes, objects, applets, macros, etc., depending on the software design methodology and the programming language used. In modern programming environments, there are software libraries, i.e. compilations of ready made functions, which may be utilized by the program for performing a wide variety of standard operations.

The computer program 704A, 704B, 704C, 704D may comprise four separate functional entities (which may be divided into modules, subroutines, methods, classes, objects, applets, macros, etc.):

a first entity to detect early repolarization patterns in leads of an electrocardiogram recorded from a subject if an amplitude of a J-point at a QRS complex and ST segment junction of a lead exceeds a predetermined amplitude threshold;

a second entity to determine amplitude patterns of ST segments in leads of the electrocardiogram; and a third entity to predict an elevated risk for a future cardiac death of the subject on the basis of a possible arrhythmia if early repolarization patterns are detected in at least two leads of the electrocardiogram, and if the ST segments in the at least two leads of the electrocardiogram are determined to have a horizontal or descending amplitude pattern.

Besides these basic entities, there may be a number of other, supplementary entities. Data 714, which comprises electrocardiogram recorded from a subject, may be brought into the working memory 712 via the non-volatile memory 710 or via the input interface 724. For this operation, there may be a further software entity. The data 708 may have been brought into the non-volatile memory 710 via a memory device (such as a memory card, an optical disk, or any other suitable non-volatile memory device) or via a telecommunications connection (via Internet, or another wired/wireless connection). The input interface 724 may be a suitable communication bus, such as USB (Universal Serial Bus) or some other serial/parallel bus, operating in a wireless/wired fashion. The input interface 724 may be directly coupled with an electronic system (electrocardiograph) recording electrocardiogram, from a subject via skin electrodes, or there may be a telecommunications connection between the input interface 724 and the electronic electrocardiography recording system. A wireless connection may be implemented with a wireless transceiver operating according to the GSM (Global System for Mobile Communications), WCDMA (Wideband Code Division Multiple Access), WLAN (Wireless Local Area Network) or Bluetooth® standard, or any other suitable standard/non-standard wireless communication means.

To conclude, the apparatus 700 is capable of analyzing electrocardiogram in real-time, i.e. during the recording, or in non-real-time, i.e. any time after completing the recording, and the electrocardiogram may be brought into the apparatus 700 by any means for transferring data.

Figure 1:
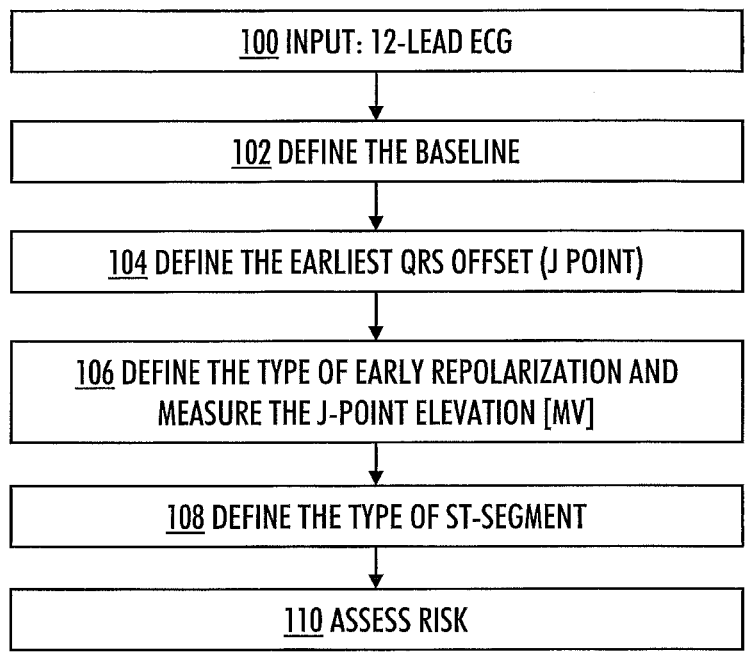
FIGS. 1, 2, 3, 4, 5, and 6 illustrate processing of an electrocardiogram.

FIG. 1 illustrates the way the computer program 704A/704B/704C may operate. In 100, the preprocessed digital 12-lead ECG is read in. In 102, the baseline for each of the 12 leads is determined, and, in 104, the earliest J-point is located. In 106, the J-point amplitude is measured from baseline, and the J-point of each ECG lead is categorized into one of the following five categories: negative, notch, slurred, discrete, and indeterminate. In 108, the ST-segment of each lead is categorized into ascending or horizontal/descending ST segment. If less than two leads are found ER positive in each subset of leads (lateral [I, aVL, V4-6], inferior [II, III, aVF] or anterior [V1-V3]), the ECG is classified as ER negative. However, if two or more leads are found ER positive in the same subset of leads, the dominant ER and ST segment type is determined for those leads (e.g. Inferior notch, horizontal ST-segment). The ECG can be scored positive for one, two or all locations (e.g. inferior+lateral, inferior+lateral+anterior, anterior+lateral etc.). When the ER and ST-segment type are determined, the patient's risk for cardiac and sudden cardiac death may be assessed in 110.

The signal may be from a standard 12-lead electrocardiogram (ECG), sampled preferably at 500 Hz or at higher sampling frequency, and consisting of at least a single cardiac cycle. The signal may be filtered in order to avoid errors in the algorithm. However, excessive filtering should be avoided as well, as it might affect the results. In this example, averaged representative beats derived from the CardioSoft version 6.51 (General Electric Company) were used.

Figure 5:
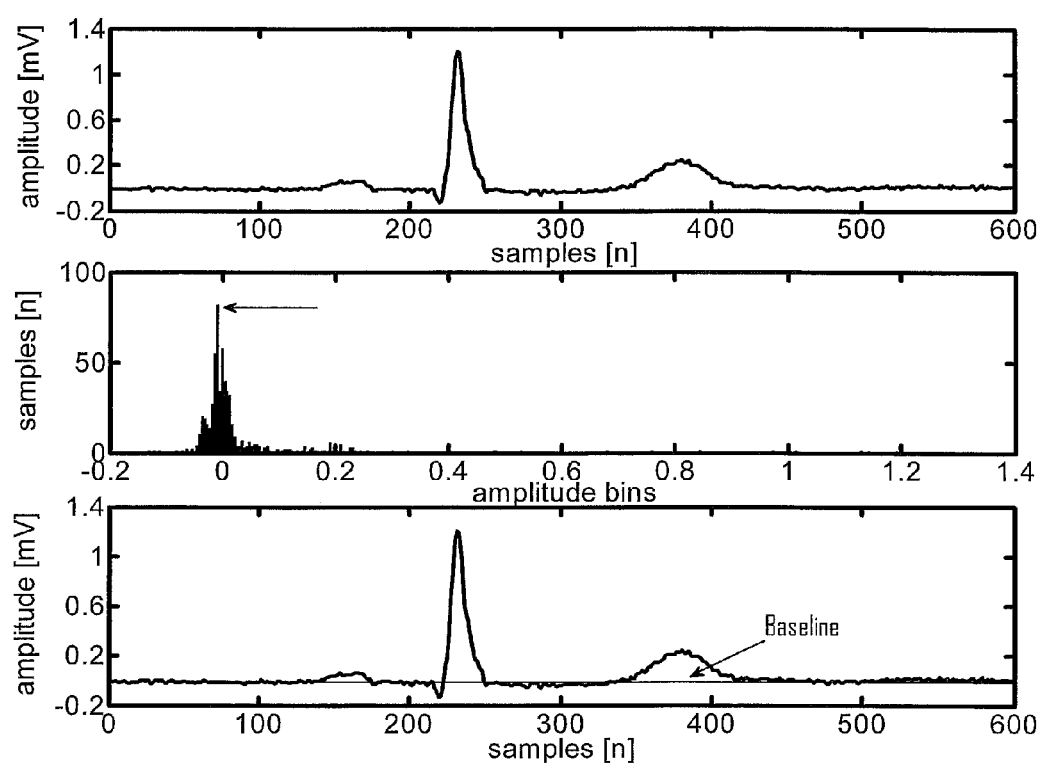

The baseline may be determined with the use of a histogram as shown in FIG. 5. First, a histogram is formed by dividing the signal amplitude span into a number of equally spaced bins (number of bins can be half of the signal length, for example) and calculating the number of samples that fall within each amplitude bin. Then, the bin that has the largest number of samples is chosen and the centre value of that bin is taken to represent the baseline for that lead. The baseline can also be determined with an average value calculated from the preceding and following T-P interval, or from the preceding P-Q interval and following P-Q interval, or from a combination of these.

Figure 2:
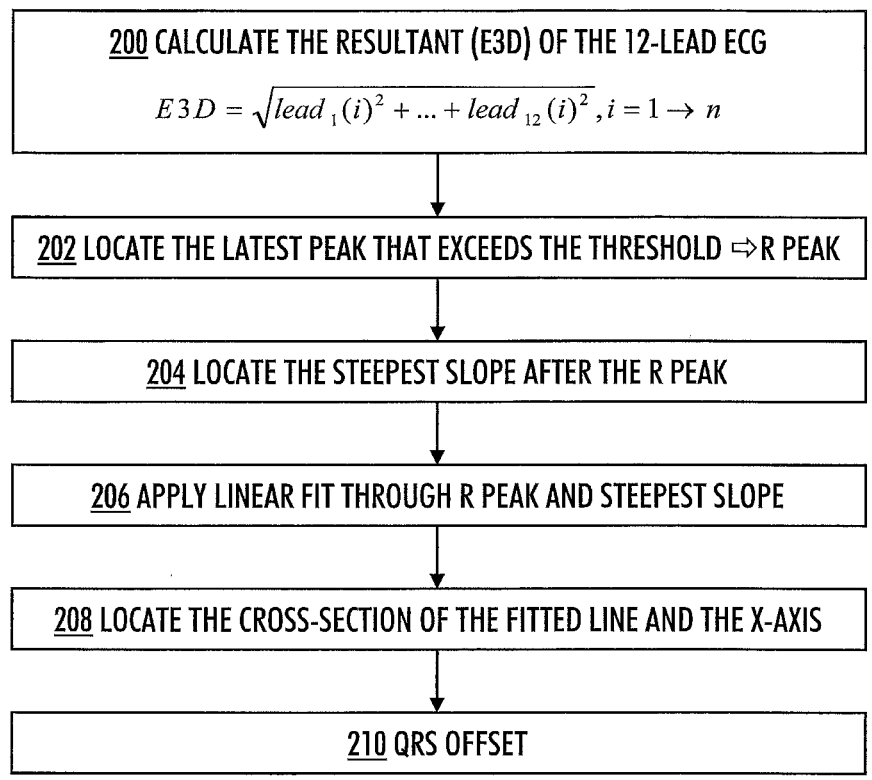

J-point can be located in many ways, by applying threshold methods to the signal or its derivative, by a geometrical analysis of the signal, by wavelet methods, by hidden Markov models and artificial neural networks, or by a combination of these, for example. Here, a simple geometrical method is presented. The earliest QRS offset is automatically determined from the cardiac cycle as shown in FIG. 2. In 200, the resultant (E3D) of the 12-lead ECG is determined as shown in equation 1.

$$E3D = \sqrt{\text{lead}_1(i)^2 + \ldots + \text{lead}_{12}(i)^2}, i=1 \to n \qquad (1)$$

Figure 6:
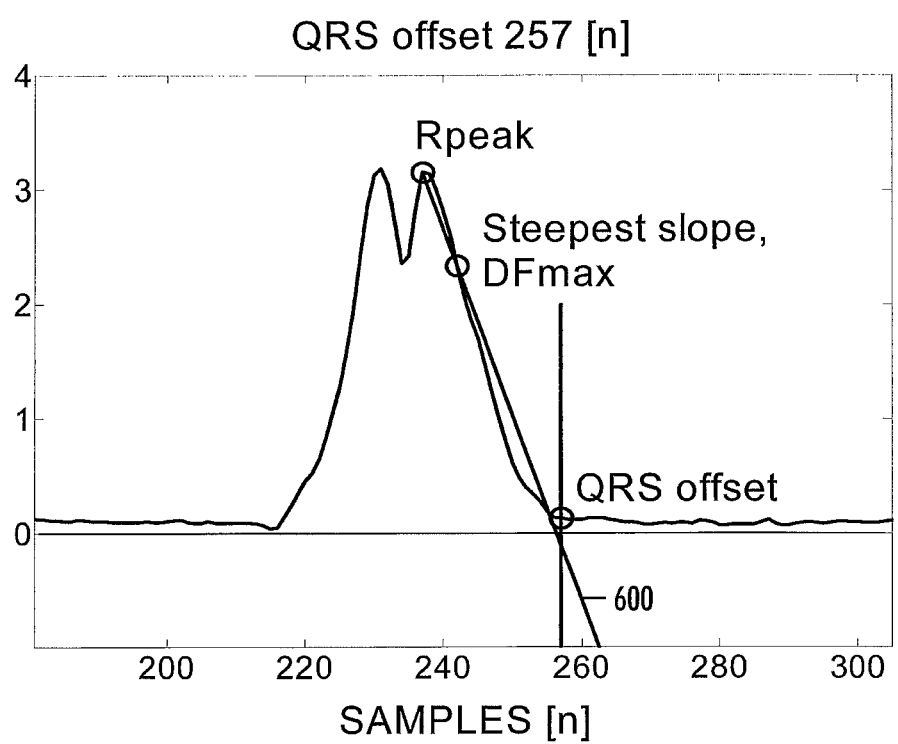

In 202 and 204, the peak and the minimum derivative, e.g. the steepest slope after the peak, are located. If the peak of the resultant is fragmented, as in FIG. 6, the latest peak that exceeds the threshold (e.g. 60% of the maximum value) is taken to represent the peak. In 206, a line 600 is fitted through the peak and the steepest slope. In 208, the cross-section of the fitted line and the X-axis is considered to represent the global QRS offset 210. Instead of fitting the line through two points, it may also be fitted through several points located near the steepest slope, e.g. through three points (adding one extra point at both sides of the steepest slope) or through a number of points that exceed a certain predefined threshold (e.g. 20% of the peak value). In this example, the minimum value of the three above-mentioned methods was used as the QRS offset.

Figure 3:
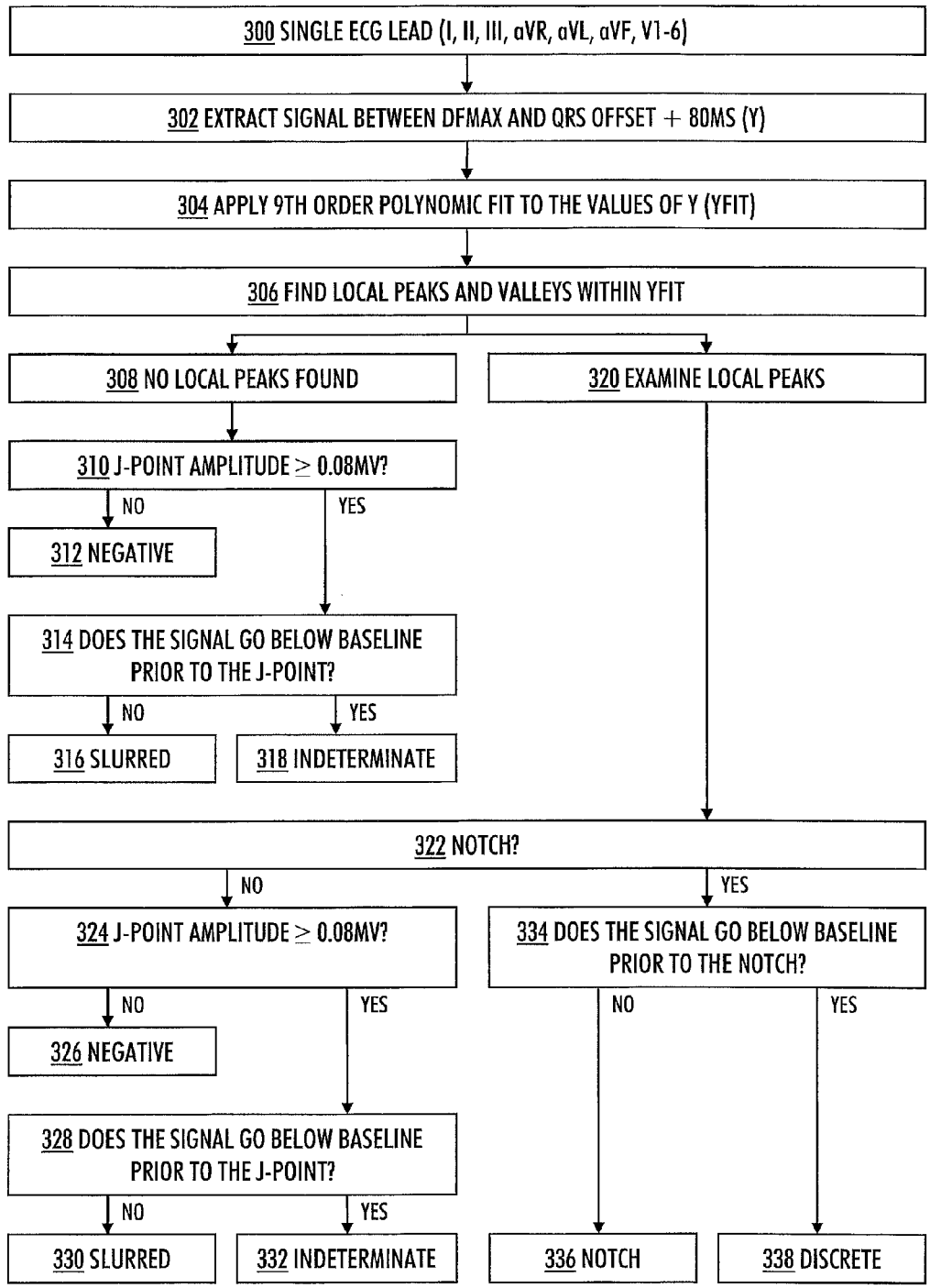

The schematic for the ER type classification is presented in FIG. 3. Each of the 12 ECG leads 300 is separately analyzed for the ER type. In 302, a segment of the signal is extracted between the steepest slope after the R-peak (DFMAX) and QRS offset+80 ms (Y). In 304, a 9th order polynomic function is fitted through the values of Y (YFIT) and the local peaks and valleys are located within the fitted values. If local peaks can be found within YFIT in 306, the peak-valley pairs are examined in 320. If the notch criteria are met by any of the peak-valley pairs in 322, the signal is considered ER positive. To further evaluate the ER type, the signal prior to the notch is examined in 334. In case it remains above the baseline, the ER type is classified as notch 336 and otherwise as discrete 338. If, however, local peaks cannot be found 308, or none of the peak-valley pairs fulfills the notch criteria in 322, the J-point elevation from the baseline is calculated in 310/324. If it is below 0.08 mV, the ER type is classified as negative 312/326. If the J-point amplitude exceeds the threshold, signal is considered ER positive. The correct ER type is then determined by examining the signal prior to the J-point in 314/328. If the signal goes below the baseline, it is classified as indeterminate 318/332, and if the signal remains above the baseline, it is classified as slurred 316/330. After classification of all 12 leads, the dominant ER-type for the inferior, anterior and lateral leads are determined.

Figure 4:
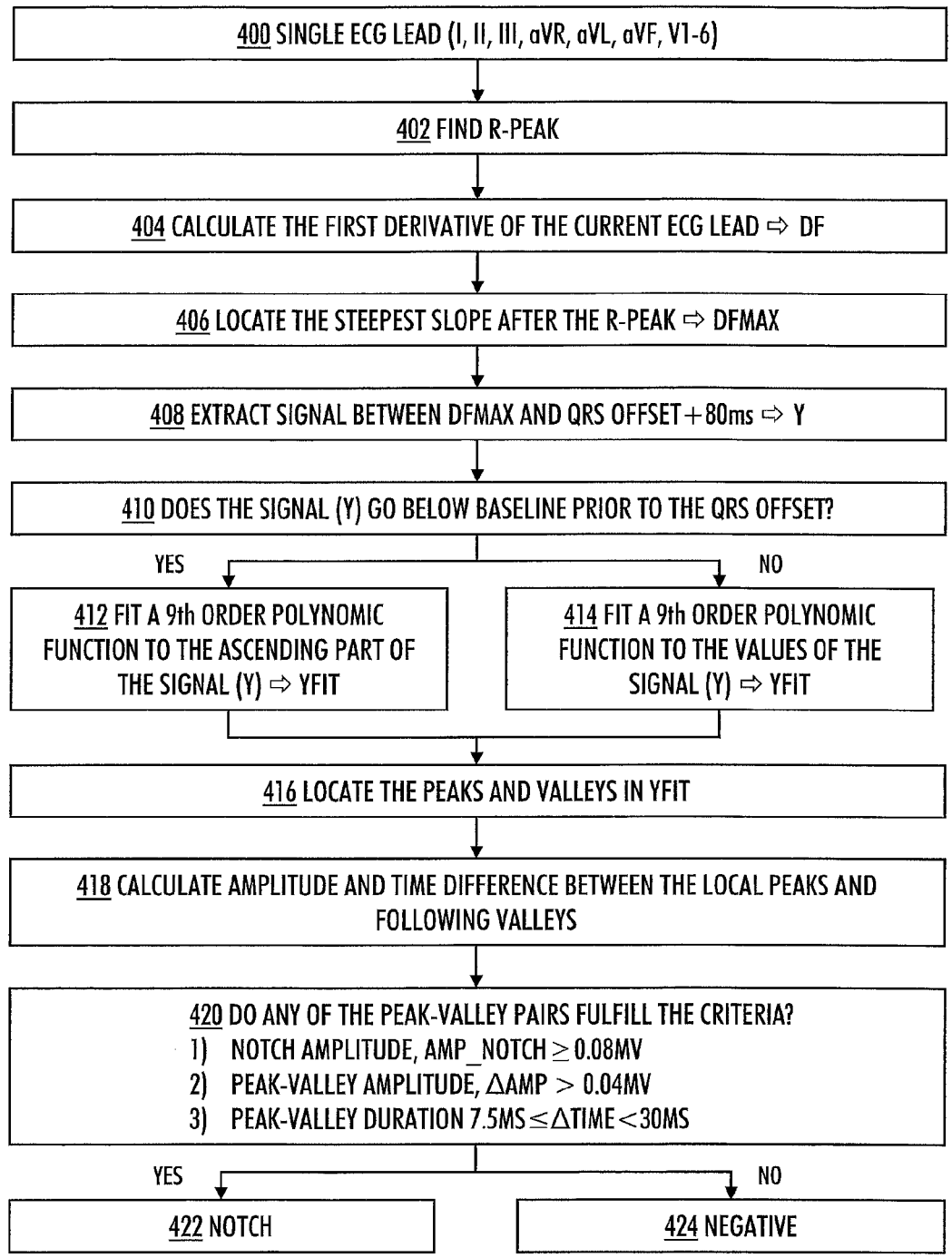

FIG. 4 illustrates the basic principle for the notch detection. All the leads 400 are studied separately. In 402, the latest peak whose absolute value exceeds the threshold (e.g. 50% of the maximum absolute value of the lead) is located. This peak is considered the R-peak. In 404, the first derivative of the lead is calculated. In 406, the steepest slope after the R-peak is located (DFMAX). In 408, signal between the steepest slope and the QRS offset+80 ms is extracted (Y). If the signal goes below baseline prior to the QRS offset in 410, the ascending part of the S-wave is located and a 9th degree polynomic function is fitted to it in 412. This is done in order to avoid excess oscillation in the fit. If the signal does not go below baseline in 410, the 9th degree polynomic function is fitted across all the values of Y, starting from the steepest slope in 414. After the fit, the local peaks and valleys in the fitted signal (YFIT) are found in 416. In 418, the amplitude and time differences are calculated between the peaks and valleys. In 420, if the amplitude difference in any of the peak-valley pairs exceeds 0.04 mV and the corresponding time difference is between 7.5-30 ms, the peak is considered to be a notch 422, otherwise, the peak is classified as normal oscillation 424.

The signal amplitude from baseline is measured at J-point+ 100 ms. It should be noted that this measurement point may vary among individuals, i.e. J-point+another predetermined number of milliseconds may be the actual point where the signal amplitude from baseline is measured. If the amplitude is greater than 0.05 mV, ST segment is classified as ascending. If the amplitude is equal or less than 0.05 mV, ST segment is classified as horizontal/descending. The ST segment of each of the 12 leads is assessed separately, and the dominant form of the ST segment is determined for the inferior, anterior and lateral leads.

Leads (II, III & aVF) are called inferior leads and leads (I, aVL and V4 to V6) are called lateral leads in ECG terminology. Chest connected leads from V1 to V6 are called also precordial leads.

An ER pattern that is either notched (a positive J deflection inscribed on the S wave) or slurred (a smooth transition from QRS to ST-segment) was first described in 1936, see Shipley & Hallaran Am Heart J1936 11:325-345.

Figure 8:
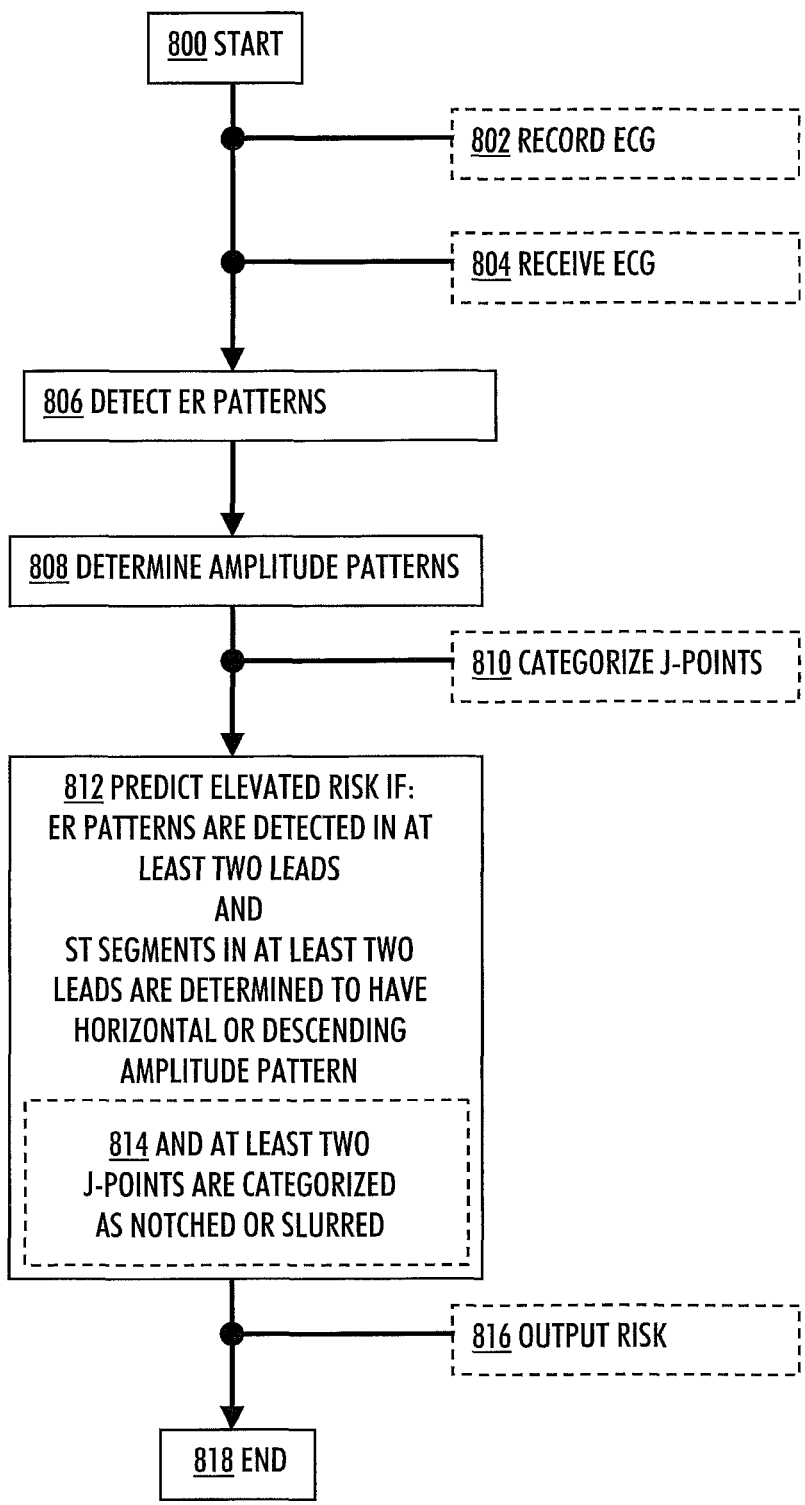
FIG. 8 illustrates embodiments of a method.

Next, with reference to FIG. 8, a method performed in an electronic apparatus is explained. The method may be implemented as the apparatus 700 or the computer program 704A comprising program instructions 706A which, when loaded into the apparatus 700, cause the apparatus 700 to perform the process to be described. The embodiments of the apparatus 700 may also be used to enhance the method, and, correspondingly, the embodiments of the method may be used to enhance the apparatus 700.

The steps are in no absolute chronological order, and some of the steps may be performed simultaneously or in an order differing from the given one. Other functions can also be executed between the steps or within the steps and other data exchanged between the steps. Some of the steps or part of the steps may also be left out or replaced by a corresponding step or part of the step.

The method starts in 800.

Optionally, in 802, the electrocardiogram is recorded from the subject with electrodes coupled to an electrocardiograph of the electronic apparatus.

Optionally, in 804, the electrocardiogram recorded from the subject is received by the electronic apparatus.

In 806, early repolarization patterns in leads of an electrocardiogram recorded from a subject are detected if an amplitude of a J-point at a QRS complex and ST segment junction of a lead exceeds a predetermined amplitude threshold.

In 808, amplitude patterns of ST segments in leads of the electrocardiogram are determined.

In 812, an elevated risk for a future cardiac death of the subject on the basis of a possible arrhythmia is predicted if early repolarization patterns are detected in at least two leads of the electrocardiogram, and if the ST segments in the at least two leads of the electrocardiogram are determined to have a horizontal or descending amplitude pattern.

In an embodiment, the J-points in leads where early repolarization patterns were detected are categorized in 810, and the prediction of 812 is positive provided that, besides the two other conditions being tested positive, the J-points in the at least two leads of the electrocardiogram are categorized as notched or slurred.

Optionally, in 816, the predicted elevated risk for the future cardiac death of the subject is outputted with an output interface of the electronic apparatus.

The method ends in 818. The method may be performed in a linear fashion, i.e. in such a manner that the required operations 806-808-812 are performed in a sequence, possibly augmented by other operations 802/804/810/814/816, as shown in FIG. 8. Alternatively, the method may be performed iteratively, i.e. in such a manner that the required operations 806-808-812 are performed once, possibly augmented by other operations 802/804/810/814/816, and, subsequently, for a number of times, until the result (=the prediction) is ready. It may be so that the quality of the prediction is estimated during the processing, and only until a required quality level is reached, the method will be ended with the result. The quality level may be calculated continuously, or after each processing round 806-808-812, or after some other processing stage. The quality level may measure the quality of the data, or the reliability of the data (=number of correctly analyzed samples, for example).

We will conclude with a study including examples and statistical analysis of the results with reference to FIGS. 9, 10, 11, 12, 13, 14, and 15. This study is not intended to restrict the embodiments, but to serve as a tool offering a deeper understanding of the subject matter, and even offering further definitions for the embodiments. The following description of background art may include insights, discoveries, understandings or disclosures, or associations together with disclosures not known to the relevant art prior to the present invention but provided by the invention. Some such contributions of the invention may be specifically pointed out below, whereas other such contributions of the invention will be apparent from their context.

As was known already before, early repolarization (ER) in inferior/lateral leads of standard ECGs increases the risk of arrhythmic death. In the study, the hypothesis that variations in ST-segment characteristics following the ER waveforms may have prognostic importance was tested.

In the study, ST-segments following ER were classified as horizontal/downsloping (Type I) or rapidly ascending/upsloping (Type II), i.e.

Type I ER=Terminal QRS notching/slurring and dominant horizontal/descending ST-segment; and Type II ER=Terminal QRS notching/slurring and dominant rapidly ascending ST-segment.

In studies of young athletes from Finland (n=62) and the United States (US) (n=503), ST-segments were classified among those with ER. Subsequently, ECGs from a general population of 10,957 middle-aged subjects were analyzed to assess the prognostic modulation of ER-associated risk by ST-segment variations.

As a result of the study, ER was observed in the inferior/lateral leads in 27/62 (44%) of the Finnish athletes. All but one of them (96%) had a Type II ST variant. A similar distribution was observed in athletes from the US. Subjects from general population with an ER≧0.1 mV and Type I ST variant (n=412) had an increased relative risk (RR) of arrhythmic death (RR 1.43; 95% CI; 1.05-1.94). When modeled for higher amplitude ER (>0.2 mV) in inferior leads and Type I ST-segment variant, the RR of arrhythmic death increased to 3.14 (95% CI 1.56-6.30). However, in subjects with Type II ST variant that dominated the athlete populations, RR for arrhythmic death was not increased (0.89, 95%; CI 0.52-1.55, NS).

The two main conclusions of the study were:
1) ST-segment morphology variants associated with ER separates subjects with and without an increased risk of arrhythmic death in the general population; and
2) Rapidly ascending ST-segments after the J-point, the dominant ST pattern in healthy athletes is a benign variant of ER.

Early repolarization (ER) patterns in standard 12-lead electrocardiograms (ECG) recorded from normal subjects was considered a benign variant (Klatsky A L, et al., "The Early Repolarization Normal Variant Electrocardiogram: Correlates and Consequences," Am J. Med. 2003; 115: 171-177) prior to two recent case-control reports associating vulnerability to idiopathic ventricular fibrillation (VF) with ER patterns in the infero-lateral leads (Haissaguerre M., et al., "Sudden Cardiac Arrest Associated With Early Repolarization," N Engl J Med. 2008; 358: 2016-2023; Nam G B, et al., "Augmentation of J Waves and Electrical Storms In Patients With Early Repolarization," N Engl J. Med. 2008; 358: 2078-2079). Subsequently, J-point elevation in leads other than V1-V3 has been identified as a predictor of cardiac and arrhythmic deaths in two independent general population cohorts, especially when present in the inferior ECG leads (Tikkanen J T, et al., "Long-Term Outcome Associated With Early Repolarization On Electrocardiography," N Engl J Med. 2009; 361: 2529-2537; Sinner M F, et al., "Association Of Early Repolarization Pattern On ECG With Risk Of Cardiac And All-Cause Mortality: A Population-Based Prospective Cohort Study (MONICA/KORA), PLoS Med. 2010; 7: e1000314). These observations have alerted physicians to consider the potential significance of such ECG variations in apparently healthy subjects, but it is not yet clear whether specific variants of ER in inferior and/or lateral leads are associated with increased risk of life-threatening arrhythmias, either alone or in conjunction with acquired structural disease states.

Besides the general population and those with documented idiopathic VF, ER and ST segment changes in precordial leads are known to be common in trained athletes. (Pelliccia A, et al., "Prevalence of Abnormal Electrocardiograms in a Large, Unselected Population Undergoing Pre-Participation Cardiovascular Screening," Eur Heart J. 2007; 28: 2006-2010; Bianco M, et al., "Does Early Repolarization in the Athlete Have Analogies with the Brugada Syndrome?," Eur Heart J. 2001; 22: 504-510; Bjornstad H, et al., "Electrocardiographic Findings According to Level of Fitness and Sport Activity," Cardiology. 1993; 83: 268-279; Crouse S F, et al., "Electrocardiograms of Collegiate Football Athletes," Clin Cardiol. 2009; 32: 37-42). In addition, ER patterns in the inferior and lateral leads with a rapidly ascending slope of the ST segment after the J-point, which resemble those observed in lead V1-V3 in athletes, are common in young healthy subjects (Klatsky A L, et al., "The Early Repolarization Normal Variant Electrocardiogram: Correlates and Consequences," Am J Med. 2003; 115: 171-177). Therefore, we hypothesized that this ER-ST segment pattern may be a benign variant of ER and performed a pilot study in young healthy athletes in Finland to assess the prevalence and patterns of ER in these subjects. We subsequently re-analyzed the ECGs from a sample of 10,957 subjects from our general population with a long follow-up (Tikkanen J T, et al., "Long-Term Outcome Associated With Early Repolarization On Electrocardiography," N Engl J Med. 2009; 361: 2529-2537) to assess the prognostic significance of different ST segment patterns in the presence of ER. Finally, the prevalence of various ER-ST segment patterns was analyzed in a second set of college athletes in the United States to validate and expand the observations in Finnish athletes.

Three study populations were used: pilot study in athletes, general middle-aged population, and athlete validation population.

Pilot Study in Athletes.

In a pilot study, ECGs were recorded from 62 young Finnish male athletes, aged 13-15 years (mean age 13.4±0.6). The tracings were analyzed for general electrocardiographic features, and for the presence of ER and patterns of ST segments following ER. The ECG characteristics of these subjects are presented in FIG. 9. ER in the inferior and/or lateral leads was present in 27 of the 62 subjects (43.5%). In all but one of the subjects with ER, the ST segment patterns following J-point elevations, defined as >0.1 mV elevation of ST-segment 100 ms after the J-point (ER Type II, see FIG. 13), were characterized by rapidly ascending ST-segments. This definition was used in subsequent analysis of prognostic significance of Type II and Type I ER (see below) and in the validation study.

General Middle-Aged Population.

This study population consists of subjects participating in the Finnish Social Insurance Institution's Coronary Heart Disease Study (CHD Study) who had undergone clinical baseline examinations between 1966 and 1972. The CHD Study was part of a large, prospective Mobile Clinic Health Survey. This cohort consisted of 10,957 men and women, age 30 to 59 years (males 52.3%) at entry, drawn from 35 different geographical areas of Finland, and was a representative sample of the middle-aged Finnish population. We excluded 93 electrocardiograms that had missing data or were otherwise unreadable. Thus, our final study group included 10,864 subjects (52% of whom were men; mean age, 44.0±8.5 years) from the original cohort. A detailed account of the study rationale and procedures performed at the baseline examination has been described previously in detail (Reunanen A, et al., "The Social Insurance Institution's Coronary Heart Disease Study. Baseline Data and 5-Year Mortality Experience, Acta Med Scand Suppl. 1983; 673: 1-120).

Athlete Validation Population.

The results in the Finnish athletes and general population were compared to findings in a population of 503 competitive athletes from the University of Miami (Miami, Fla.). FIG. 10 illustrates the characteristics of the athletes in the Miami validation population. Fifty-one percent were males, with ages ranging from 17-24 years, and 34% were African-American, compared to 100% male and no athletes of African descent in the Finnish athletes (see FIGS. 9 and 10).

The presence of ER was analyzed from standard resting 12-lead ECGs, recorded at a paper speed of 50 mm per second and calibration of 1 mV per 10 mm, using the criteria of J-point elevation≧0.1 mV in at least two inferior or lateral leads (Haissaguerre M., et al., "Sudden Cardiac Arrest Associated With Early Repolarization," N Engl J Med. 2008; 358: 2016-2023). Each ECG positive for ER was classified according to specific ER patterns, with coding as: 1) notched, 2) slurred, or 3) undetermined (no dominant form). Notching was defined as a positive J deflection at the end of the QRS complex, and slurring as a terminal slower waveform transitioning from QRS J-point to the ST-segment.

ST-segment patterns after the J-point were coded as follows: 1) horizontal/descending (Type I), or 2) concave/rapidly ascending (Type II). The concave/rapidly ascending ST-segment was defined as >0.1 mV elevation of ST-segment within 100 ms after the J-point or a persistently elevated ST segment of >0.1 mV throughout ST-segment. These criteria were derived from the findings in the ER-ST segment patterns in the healthy Finnish athletes described above. Horizontal/descending type was defined as ≦0.1 mV elevation of the ST-segment within 100 ms after the J-point. The isoelectric line (baseline) was defined as the level between two T-P intervals. J-point or ST-segment patterns had to be present in at least two inferior or lateral leads for positive grading. Examples of Type I and Type II ER ECGs are illustrated in FIGS. 13 and 14.

Figure 13:

FIG. 13 shows ECGs of two young athletes, A and B, with ER and the common ST-segment morphology. All subjects presenting early repolarization pattern in the athlete pilot study population had similar rapidly ascending ST-segment after the J-point. Both terminal QRS notching and slurring were present, but none of the 12 cases with ER had dominant ST-segment categorized as horizontal/descending. Black arrows in FIG. 13 indicate terminal QRS notching or slurring.

Figure 14:
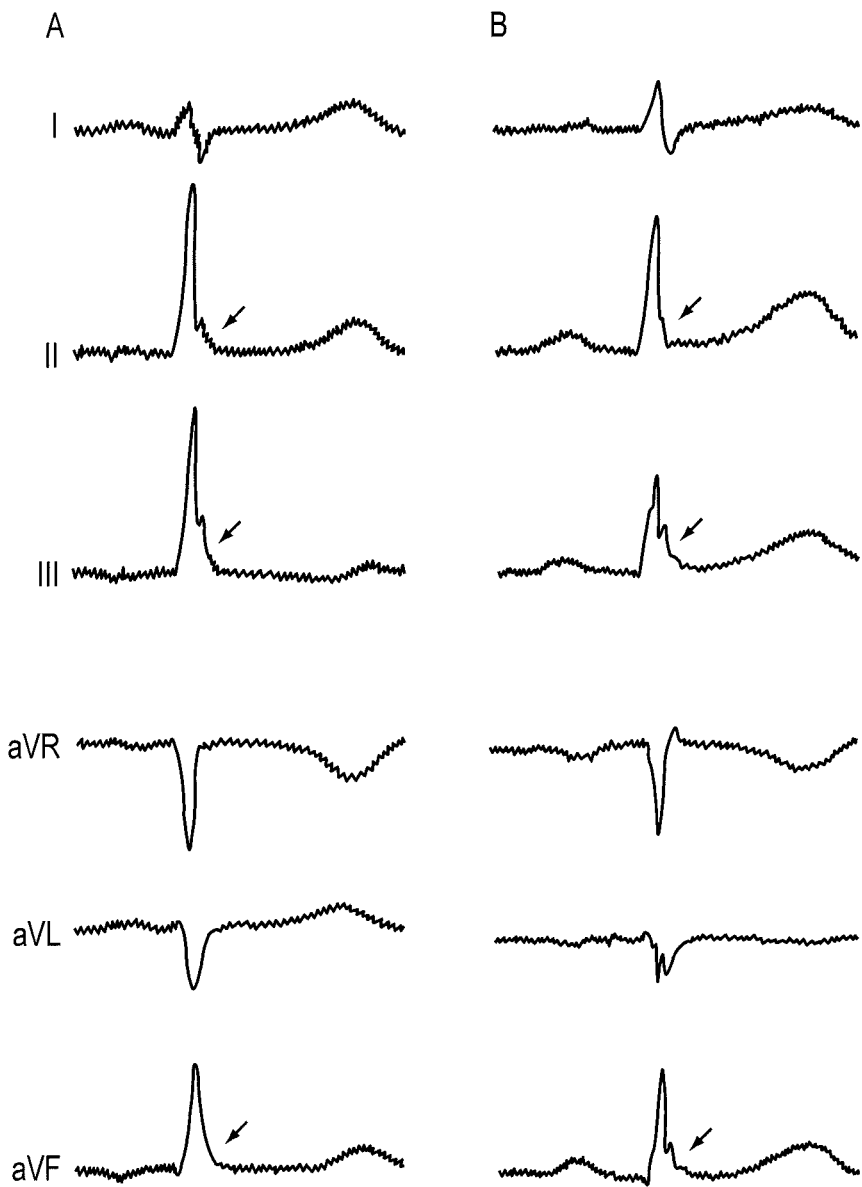

FIG. 14 shows ST-segment patterns from two subjects in the general population sample. Subject A presented type I ER (dominant horizontal ST-segment in leads II and aVF and descending ST-segment in lead III), whereas subject B presented type II ER (rapidly ascending ST-segment in leads II, III, aVF). In the middle-aged general population only type I ER predicted arrhythmic death. Black arrows in FIG. 14 indicate terminal QRS notching or slurring.

The general population subjects were followed up for a mean of 30±11 years (until Dec. 31, 2007) after the baseline examinations performed between 1966 and 1972. The mortality data was determined from the Causes of Death Register maintained by Statistics Finland. Less than 2% of subjects were lost to follow-up as a result of moving abroad, but even in this group, the survival status could still be determined for a majority of subjects. Because of extensive administrative registers in Finland, every death in the country is recorded, and the quality and reliability of these registers have been validated earlier (Pajunen P, et al., "The Validity of the Finnish Hospital Discharge Register and Causes of Death Register Data on Coronary Heart Disease," Eur J Cardiovasc Prev Rehabil. 2005; 12: 132-137). To identify cases of sudden death from arrhythmia, all deaths from cardiac causes were reviewed by experienced cardiologists (OA, HVH) based on the definitions presented in the Cardiac Arrhythmia Pilot Study (Greene H L, et al., "Classification of Deaths After Myocardial Infarction as Arrhythmic or Nonarrhythmic (the Cardiac Arrhythmia Pilot Study)," Am J Cardiol. 1989; 63: 1-6), as described by our group previously (Tikkanen J T, et al., "Long-Term Outcome Associated With Early Repolarization On Electrocardiography," N Engl J Med. 2009; 361: 2529-2537). The endpoint of this study was arrhythmic death.

Figure 15:
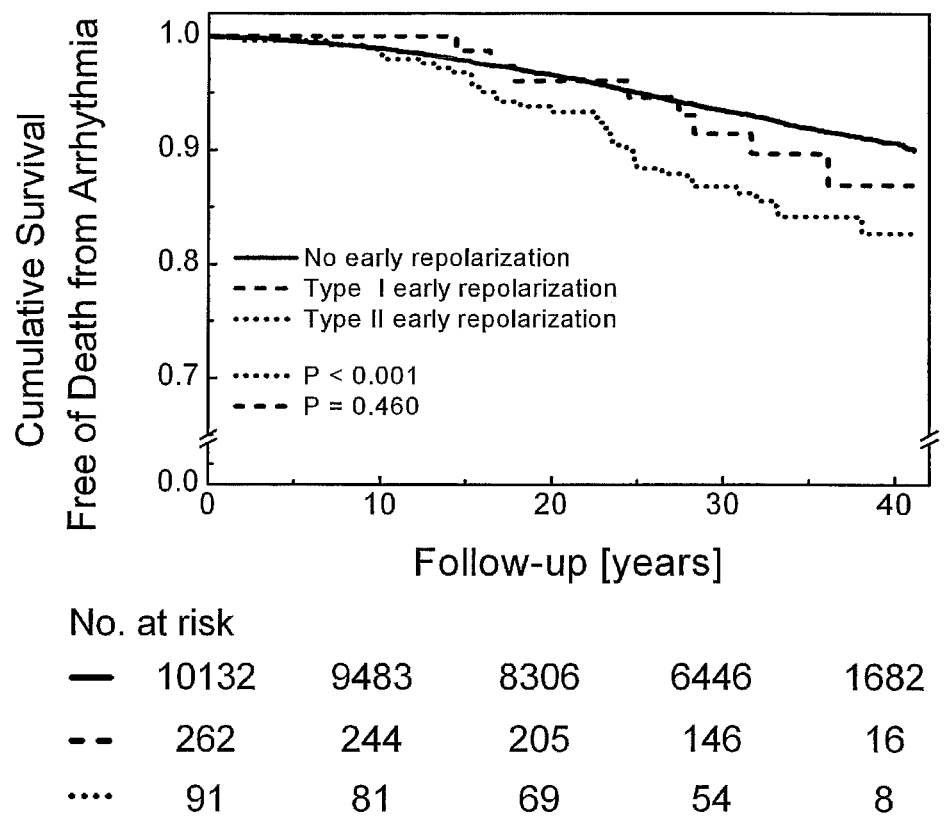

Statistical analysis is shown in FIG. 15. All continuous data is presented as mean±SD. The general linear model was used to compare the age- and sex-adjusted mean values for continuous variables and the prevalence of categorical variables between the groups. The hazard ratios and 95% confidence intervals for death were calculated using Cox proportional hazards model. The primary adjustments to these models were age and gender. Kaplan-Meier survival curves were plotted for different ER types. Statistical analyses were performed with SAS software, version 9.1.3 (SAS Institute) and with the Statistical Package for Social Studies, version 17.0 (SPSS). P value of less than 0.05 was considered to indicate statistical significance.

The results of the study may be presented under the following topics numbered from 1 to 6.

1. Prevalence and Patterns of ER in the Middle-aged General Population

Early repolarization in inferior and/or lateral leads was present in 576 subjects (5.3%) in the general middle-aged population. The distribution of J-point types was notched in 228 subjects (39.6% of those with ER), slurred in 292 (50.7% of those with ER), and undetermined in 56 subjects (9.7% of those with ER). Distribution of ST-segments was as follows: [1] horizontal/descending Type I ER in 412 subjects (71.5%), and [2] concave/rapidly ascending Type II ER in 164 subjects (28.5%).

2. Characteristics of General Population Subjects with ER Based Upon ST-Segment Patterns The baseline characteristics of general population subjects, based upon the specific ER-ST segment patterns, are presented in FIG. 11. FIG. 11 illustrates the characteristics of subjects with ER and Type I and Type II ST segment patterns. A subtle male dominance was present among the subjects with Type I ER-ST segments. This group was older, and the QRS duration in ECG longer, compared to those without ER. Other characteristics did not differ between these groups. In contrast, subjects with Type II ER were younger, more often males, had lower body mass index, lower heart rate, lower blood pressure, shorter QTc duration, had higher prevalence of electrocardiographic left ventricular hypertrophy, and were more commonly smokers compared to those without ER.

3. Assessment of Mortality According to ER Pattern

Analysis of outcomes among subjects with notched ER≧0.1 mV, independent of ST-segment patterns, had age- and sex adjusted RR of 1.58 (CI 1.07-2.32, p=0.05) for arrhythmic death. The relative risk of arrhythmic death in subjects with slurred ER patterns≧0.1 mV, independent of ST-segment patterns, was 1.19 (CI 0.81-1.76, p=0.41). In subjects with >0.2 mV ER, independent of ST-segment patterns, the numbers were conflicting, as notched >0.2 mV ER had adjusted RR of 2.14 (CI 0.89-5.16) and slurred >0.2 mV ER a very high RR of 5.14 (CI 1.92-13.76). Before adjustments, both notching and slurring of the terminal QRS conveyed significantly increased risk. When only inferior location was included, subjects with notched ER had adjusted RR of 1.54 (CI 1.00-2.38) and subjects with slurred ER had adjusted RR of 1.50 (CI 0.95-2.37), with borderline significance. In rest of the comparisons, the results were contradictory as no clear difference between notching or slurring of the terminal QRS was observed, see FIG. 11.

4. Risk of Arrhythmic Death with ER Stratified for Type I and Type II ST Segment Patterns During follow-up, 6,133 subjects (56.5%) died. Of these deaths 1969 (32.1% of all deaths) were from cardiac causes, and 795 (40.5%) of these were classified as sudden arrhythmic deaths. FIG. 12 presents unadjusted and age- and sex-adjusted relative risks (RR, 95% CI) of death from arrhythmia associated with different ER-ST segment patterns.

Subjects with ER and Type I ST segments (horizontal or downsloping) had a higher risk of sudden arrhythmic death (age- and sex adjusted relative risk [RR] 1.43; 95% confidence interval [CI] 1.05-1.94) than did subjects without ER. In contrast, subjects with ER and Type II ST segments (upsloping) (n=164), did not have an elevated risk for arrhythmic death (adjusted RR 0.89, CI 0.52-1.55).

A separate analysis of inferior ER subjects demonstrated same trend. Among subjects with inferior ER and Type I ST segments (n=275), the RR was 1.72 (CI 1.22-2.41) for arrhythmic death after adjustments for age and gender. By contrast, inferior ER and Type II ST segments (n=90) was not associated with adverse outcome, see FIG. 12.

5. Early Repolarization and ST-Segment Patterns in Healthy Finnish Athletes

ER in the inferior and/or lateral leads was present in 27 of the 62 subjects (43.5%) in the pilot study of young athletes. As anticipated, there were no outcome events in this group, as this study was intended to seek only cross-sectional observations of ER prevalence and ST-segment patterns. In all but one of the subjects with ER (96%), the ST segment patterns following J-point elevations, were Type II, defined as >0.1 mV elevation of ST-segment 100 ms after the J-point with an ascending slope (see FIG. 13). This paralleled the benign subset in the general population.

6. Validation Data from College Athletes in the United States.

In the validation population of 503 athletes from University of Miami, 30% of the athletes had inferior or lateral ER (inferior 21%, lateral 20%, 10% both). Among the athletes with ER, the proportion with concave/rapidly ascending ST-segments (Type II) was 85%. Thus the cumulative prevalence of inferior and lateral ER with horizontal or descending ST-segments (Type I) in the athlete population was 3.5% and inferior ER followed by horizontal or descending ST-segments was only 3.0%.

Finally, discussion of the study will follow.

The results of this study suggest that ER patterns in the inferior or lateral leads of a standard 12-lead ECG are not associated with uniformly increased risk of arrhythmic death in a middle-aged general population. ER patterns associated with horizontal or downsloping ST-segments after the J-point are accompanied by an increased risk for arrhythmic death, but ER followed by rapidly upsloping ST-segments after the J-point was not associated with increased risk of arrhythmic death. The highest risk occurred with the combination of ER in the inferior limb leads, high amplitude (>0.2 mV) J-point waveforms, and a dominant horizontal or descending ST-segment after the J-point. The combination of a high amplitude slurred inferior ER, with dominant horizontal or descending ST-segments was associated with an adjusted relative risk of arrhythmic deaths of 5.26 (1.97-14.07) relative to no ER. None of the lateral patterns of ER without concomitant J-point elevation in inferior leads was associated with increased mortality.

In addition to different prognostic impact, the subjects with various types of ST-segment after the ER had certain differences in the baseline characteristics. Those with a rapidly ascending S-T segment pattern were younger, their heart rate and blood pressure were lower and they more commonly had ECG signs of left ventricular hypertrophy. In contrast, subjects with Type I (horizontal or downsloping) S-T segment pattern with ER were somewhat older and had longer QRS durations, but did not differ in other characteristics from those without ER. Overall, these characteristics suggest that those subjects with rapidly ascending ST-segments were healthier and likely more physically active than the others.

The benign implications of the rapidly upsloping ST-segment pattern in association with ER in the general middle-aged population may have implications for interpretation of ER in apparently healthy athletes. In both the pilot and validation athlete sets, the pattern associated with low relative risk in the general population with long-term follow-up dominated in prevalence, consistent with the notion that ER in athletes is generally benign, although exceptions may exist (Cappato R, et al., "QRS Slurring, and ST Elevation in Athletes With Cardiac Arrest in the Absence of Heart Disease: Marker of Risk or Innocent Bystander?," Circ Arrhythm Electrophysiol. 2010; 3: 305-311). In addition, the finding in Finnish athletes was validated in a multiracial athlete population from the United States with a more diverse ethnic make-up. Specifically, the distribution of different ST-segment characteristics in conjunction with ER was similar, and low prevalence of ER with horizontal/descending ST-segment, was nearly identical between the two athlete populations and to that of the general population in the present study. The prevalence of ascending Type II ST-segments was almost equally prevalent in young healthy Finnish and American athletes.

Terminal left precordial QRS notching has been previously reported to be more prevalent in malignant than benign variants of ER (idiopathic VT/VF) in a single institution cohort (Merchant F M, et al., "Ability of Terminal QRS Notching to Distinguish Benign From Malignant Electrocardiographic Forms of Early Repolarization," Am J Cardiol. 2009; 104: 1402-1406). However, definite differences between prognostic significance of notching and slurring of ER pattern did not emerge in the present population. When all ER cases were pooled together, subjects with a notched J-point had worse prognosis, but in other comparisons the results were not unambiguous. Slurred morphology with a high J-point amplitude in inferior localization was associated with the highest risk of arrhythmic death in combination with the horizontal/descending ST-segment.

We used a specific pre-defined measuring point (100 ms at baseline level after J-point) for coding of ST segment based on observations from the pilot study population. This point may not be optimal for separating the malignant and benign forms of ER syndrome and should be tested also in other populations, such as those with documented ventricular fibrillation. Despite the arbitrary empiric measuring point, the results confirm the primary hypothesis of the study. A recent study also partly confirms the present observations showing that the presence of J-wave with no ST-segment elevation (>0.05 mV) was more prevalent in athletes with cardiac arrest or sudden death than in control healthy athletes (Cappato R, et al., "QRS Slurring, and ST Elevation in Athletes With Cardiac Arrest in the Absence of Heart Disease: Marker of Risk or Innocent Bystander?," Circ Arrhythm Electrophysiol. 2010; 3: 305-311). The present findings are also partly in line with those observed in Brugada syndrome, where the saddleback-type ECG patterns (types II and III) have been shown to be benign forms of Brugada ECG, but ST segment elevation with descending slope (type I) is more malignant (Matsuo K, et al., "The Prevalence, Incidence and Prognostic Value of the Brugada-type Electrocardiogram: A Population-based Study of Four Decades," J Am Coll Cardiol. 2001; 38: 765-770; Miyasaka Y, et al., "Prevalence and Mortality of the Brugada-type Electrocardiogram in One City in Japan," J Am Coll Cardiol. 2001; 38: 771-774; and Junttila M J, et al., "Prevalence and Prognosis of Subjects with Brugada-type ECG Pattern in a Young and Middle-aged Finnish Population," Eur Heart J. 2004; 25: 874-878). It is also possible that the different ST-segment types defined in this study of subjects with ER are a spectrum of the same electrophysiological abnormality manifested in various forms at different times, similar to that observed in Brugada syndrome, where Brugada ECG types II and III can convert spontaneously to type I, e.g. during fever, or by some drugs blocking the sodium channels (Antzelevitch C, et al., "Brugada Syndrome: Report of the Second Consensus Conference," Heart Rhythm. 2005; 2: 429-440).

The observations from the present community-based study show that the ER with rapidly ascending ST segment in inferior or lateral leads of a 12-lead ECG is a benign variant, similar to that observed in leads V1-V3, at least in middle-aged subjects. Subjects with this ECG pattern should not be profiled at high risk, and would not require specific cardiovascular evaluations or treatment, if they are asymptomatic without a family history of sudden cardiac death or serious arrhythmias. In contrast, a specific ER pattern in inferior leads of a standard 12-lead ECG with a horizontal/descending ST-segment appears to be associated with an increased risk of arrhythmic death and a high amplitude of J-point elevation increases the risk even further. Further studies on the pathophysiological mechanisms of this ECG pattern and strategies to treat the subjects with this ECG abnormality are needed in the future. Among the questions to be explored are whether the high risk ER-ST segment pattern reflects a primary arrhythmic syndrome, or if a modifying factor for specific arrhythmic risk in patients with acquired structural heart disease. The temporal distribution of risk observed in our original general population study (Tikkanen J T, et al., "Long-Term Outcome Associated With Early Repolarization On Electrocardiography," N Engl J Med. 2009; 361: 2529-2537) suggests the possibility of the latter.

While this invention has been particularly shown and described with references to example embodiments thereof, it will be understood by those skilled in the art that various changes in form and details may be made therein without departing from the scope of the invention encompassed by the appended claims.

What is claimed is:

1. An apparatus comprising a processor configured to:
   detect early repolarization patterns in leads of an electrocardiogram recorded from a subject if an amplitude of a J-point at a QRS complex and ST segment junction of a lead exceeds a predetermined amplitude threshold;
   categorize the J-points in leads where early repolarization patterns were detected;
   determine amplitude patterns of ST segments in leads of the electrocardiogram; and
   predict an elevated risk for a future cardiac death of the subject on the basis of a possible arrhythmia if early repolarization patterns are detected in at least two leads of the electrocardiogram, and if the ST segments in the at least two leads of the electrocardiogram are determined to have a horizontal or descending amplitude pattern, and if the J-points in the at least two leads of the electrocardiogram are categorized as notched or slurred.

2. The apparatus of claim 1, wherein the leads are inferior leads II, III, and aVF of a 12-lead electrocardiogram.

3. The apparatus of claim 1, wherein the leads are lateral leads I, aVL, V4, V5, and V6 of a 12-lead electrocardiogram.

4. The apparatus of claim 1, wherein the amplitude threshold is at least one of 0.08 millivolts, over 0.08 millivolts, between 0.08 and 0.12 millivolts, 0.1 millivolt, over 0.1 millivolt, between 0.18 and 0.22 millivolts, over 0.18 millivolts, 0.2 millivolts, over 0.2 millivolts, between 0.08 and 0.22 millivolts.

5. The apparatus of claim 1, wherein the apparatus further comprises an input interface configured to receive the electrocardiogram recorded from the subject.

6. The apparatus of claim 1, wherein the apparatus further comprises an electrocardiograph configured to record the electrocardiogram from the subject with electrodes.

7. The apparatus of claim 1, wherein the apparatus further comprises an output interface configured to output the predicted elevated risk for the future cardiac death of the subject.

8. A method performed in an electronic apparatus, comprising:
   detecting early repolarization patterns in leads of an electrocardiogram recorded from a subject if an amplitude of a J-point at a QRS complex and ST segment junction of a lead exceeds a predetermined amplitude threshold;
   categorizing the J-points in leads where early repolarization patterns were detected;
   determining amplitude patterns of ST segments in leads of the electrocardiogram; and
   predicting an elevated risk for a future cardiac death of the subject on the basis of a possible arrhythmia if early repolarization patterns are detected in at least two leads of the electrocardiogram, and if the ST segments in the at least two leads of the electrocardiogram are determined to have a horizontal or descending amplitude pattern, and if the J-points in the at least two leads of the electrocardiogram are categorized as notched or slurred.

9. The method of claim 8, wherein the leads are inferior leads II, III, and aVF of a 12-lead electrocardiogram.

10. The method of claim 8, wherein the leads are lateral leads I, aVL, V4, V5, and V6 of a 12-lead electrocardiogram.

11. The method of claim 8, wherein the amplitude threshold is at least one of 0.08 millivolts, over 0.08 millivolts, between 0.08 and 0.12 millivolts, 0.1 millivolt, over 0.1 millivolt, between 0.18 and 0.22 millivolts, over 0.18 millivolts, 0.2 millivolts, over 0.2 millivolts, between 0.08 and 0.22 millivolts.

12. The method of claim 8, further comprising:
   receiving by the electronic apparatus the electrocardiogram recorded from the subject.

13. The method of claim 8, further comprising:
   recording the electrocardiogram from the subject with electrodes coupled to an electrocardiograph of the electronic apparatus.

14. The method of claim 8, further comprising:
outputting the predicted elevated risk for the future cardiac death of the subject with an output interface of the electronic apparatus.

15. A non-transitory computer readable storage medium storing a computer program, comprising program instructions which, when loaded into an apparatus, cause the apparatus
- to detect early repolarization patterns in leads of an electrocardiogram recorded from a subject if an amplitude of a J-point at a QRS complex and ST segment junction of a lead exceeds a predetermined amplitude threshold;
- to categorize the J-points in leads where early repolarization patterns were detected;
- to determine amplitude patterns of ST segments in leads of the electrocardiogram; and
- to predict an elevated risk for a future cardiac death of the subject on the basis of a possible arrhythmia if early repolarization patterns are detected in at least two leads of the electrocardiogram, and if the ST segments in the at least two leads of the electrocardiogram are determined to have a horizontal or descending amplitude pattern, and if the J-points in the at least two leads of the electrocardiogram are categorized as notched or slurred.

16. An apparatus comprising:
- means for detecting early repolarization patterns in leads of an electrocardiogram recorded from a subject if an amplitude of a J-point at a QRS complex and ST segment junction of a lead exceeds a predetermined amplitude threshold;
- means for categorizing the J-points in leads where early repolarization patterns were detected;
- means for determining amplitude patterns of ST segments in leads of the electrocardiogram; and
- means for predicting an elevated risk for a future cardiac death of the subject on the basis of a possible arrhythmia if early repolarization patterns are detected in at least two leads of the electrocardiogram, and if the ST segments in the at least two leads of the electrocardiogram are determined to have a horizontal or descending amplitude pattern, and if the J-points in the at least two leads of the electrocardiogram are categorized as notched or slurred.

* * * * *